United States Patent [19]

Zarate et al.

[11] Patent Number: 5,782,895
[45] Date of Patent: Jul. 21, 1998

[54] ILLUMINATOR FOR PHOTODYNAMIC THERAPY

[75] Inventors: Carlos E. Zarate; H. Graciela Zarate, both of Hamilton, Canada

[73] Assignee: DUSA Pharmaceuticals, Inc., Toronto, Canada

[21] Appl. No.: 466,427

[22] Filed: Jun. 6, 1995

Related U.S. Application Data

[62] Division of Ser. No. 136,831, Oct. 18, 1993, Pat. No. 5,441,531.

[51] Int. Cl.[6] ............................................. A61B 5/00
[52] U.S. Cl. .......................... 607/88; 607/90; 250/504 R; 356/216
[58] Field of Search ..................... 607/88, 90; 250/492.1, 250/504 R; 362/293, 804; 356/216–217

[56] References Cited

U.S. PATENT DOCUMENTS

| | | | |
|---|---|---|---|
| 3,711,700 | 1/1973 | Westlund, Jr. et al. | 128/665 |
| 4,240,133 | 12/1980 | Haina et al. | 362/293 |
| 4,316,467 | 2/1982 | Muckerheide | 128/303.1 |
| 4,336,809 | 6/1982 | Clark | 128/665 |
| 4,444,190 | 4/1984 | Mutzhas | 250/504 R |
| 4,523,866 | 6/1985 | Kojima et al. | 250/492.1 |
| 4,562,831 | 1/1986 | Murskoshi et al. | 128/6 |
| 4,563,589 | 1/1986 | Scheffer | 250/504 R |
| 4,573,467 | 3/1986 | Rich et al. | 128/303.1 |
| 4,641,033 | 2/1987 | Petelin et al. | 205/504 R |
| 4,644,899 | 2/1987 | Glaus | 250/504 R |
| 4,686,986 | 8/1987 | Fenyo et al. | 607/90 |
| 4,690,141 | 9/1987 | Castel et al. | 128/396 |
| 4,822,335 | 4/1989 | Kawai et al. | 604/20 |
| 4,836,203 | 6/1989 | Mueller et al. | 128/203.1 |
| 4,890,208 | 12/1989 | Izenour | 362/293 |
| 4,911,166 | 3/1990 | Leighton et al. | 607/90 |
| 4,932,934 | 6/1990 | Dougherty et al. | 604/21 |
| 4,933,816 | 6/1990 | Hug et al. | 356/318 |
| 4,951,663 | 8/1990 | L'Esperance, Jr. | 128/395 |
| 4,957,481 | 9/1990 | Gatenby | 604/20 |
| 5,010,452 | 4/1991 | Krebser et al. | 362/19 |
| 5,071,416 | 12/1991 | Heller et al. | 606/3 |
| 5,079,262 | 1/1992 | Kennedy et al. | 514/561 |
| 5,174,297 | 12/1992 | Daikuzono | 128/665 |
| 5,206,515 | 4/1993 | Elliott et al. | 250/492.1 |
| 5,211,938 | 5/1993 | Kennedy et al. | 424/7.1 |
| 5,344,434 | 9/1994 | Talmore | 607/88 |

FOREIGN PATENT DOCUMENTS

| | | |
|---|---|---|
| 1 253734 | 1/1988 | European Pat. Off. . |
| 0 478 506 | 4/1992 | European Pat. Off. . |
| 41 12 275 | 11/1992 | Germany . |
| 1 2100403 | 12/1982 | United Kingdom . |
| 1 8911260 | 11/1989 | WIPO . |

*Primary Examiner*—Robert L. Nasser
*Attorney, Agent, or Firm*—Foley & Lardner

[57] ABSTRACT

An illuminator for photodynamic therapy includes a bulb, a condenser lens assembly and a filter assembly. The filter assembly includes the following components in an optical path: (1) a high-pass filter to filter out light having wavelengths below a first wavelength value; (2) a low-pass dichroic filter to filter out light having wavelengths above a second wavelength value; and (3) a dichroic mirror which reflects light having wavelengths between the first wavelength value and the second wavelength value and which transmits infrared light. An exit lens assembly directs light transmitted through the high-pass filter and the low-pass dichroic filter and reflected by the dichroic mirror onto a patient for photodynamic therapy. The condenser lens assembly and the exit lens assembly scramble the beam to ensure that the patient is illuminated with light which is highly uniform in both intensity and spectral characteristics (color) throughout the illuminated area.

10 Claims, 10 Drawing Sheets

1
ILLUMINATOR FOR PHOTODYNAMIC THERAPY

This application is a division of application Ser. No. 08/136,831, filed Oct. 18, 1993, now U.S. Pat. No. 5,441,531.

BACKGROUND OF THE INVENTION

The invention is directed to an illuminator for photodynamic therapy, including diagnosis. More specifically, the invention is directed to an illuminator for photodynamic therapy which produces a high-powered beam at the appropriate wavelengths which is highly uniform in both intensity and spectral characteristics (color) throughout the illuminated area.

Photodynamic therapy ("PDT") or photochemotherapy is currently being used to treat several types of aliments in or near the skin or other tissues. For example, PDT is being used to treat different types of skin cancer. In PDT, a patient is administered a photo-activatable drug which accumulates in the tissue being treated. An area of the patient which includes the tissue being treated is then exposed to light. The light causes chemical and/or biological changes in the photo-activable drug which in turn selectively distinguishes, destroys or alters the target tissue while at the same time causing only mild and reversible damage to other tissues in the treatment area.

General background information on PDT using 5-Aminolevulinic acid ("ALA") can be found in U.S. Pat. No. 5,079,262, entitled "Method of Detection and Treatment of Malignant and Non-Malignant Lesions Utilizing 5-Aminolevulinic Acid," and issued to James C. Kennedy et al. on Jan. 7, 1992 and U.S. Pat. No. 5,211,938, entitled "Method of Detection of Malignant and Non-Malignant Lesions by Photochemotherapy of Protoporphyrin IX Percursors," and issued to James C. Kennedy et al. on May 18, 1993. The contents of these patents are incorporated herein by reference. ALA is a drug which functions as a prodrug in the body and metabolizes to protoporphyrin IX ("PpIX"). PpIX in cells may be photoactivated with light of a certain wavelength to either fluoresce, degrade or otherwise be altered.

For therapeutic reasons it is desirable to have a large power output which is uniform in intensity and color over a large area. In addition, it has been discovered that use of light having wavelengths between about 600 nm (nanometers) and about 700 nm is particularly advantageous for certain forms of treatment.

Unfortunately, conventional illuminators produce a relatively high percentage of light in the infrared ("IR") region. In order to prevent this high percentage of infrared radiation from harming a patient, the overall power output of the lamp must be limited. Moreover, conventional illuminators do not produce a beam which is uniform in intensity and color over a large area, e.g., greater than 10 cm (centimeters) in diameter, and do not produce light virtually entirely in the 600 nm to 700 nm wavelength range.

Accordingly, there is a real need for an improved illuminator for photodynamic therapy.

SUMMARY OF THE INVENTION

It is an object of the invention, therefore, to provide an improved illuminator for photodynamic therapy.

It is another object of the invention to provide an illuminator beam for photodynamic therapy which includes substantially no infrared light.

Another object of the invention is to provide an illuminator for photodynamic therapy which produces a very uniform beam in terms of both spectral characteristics and intensity over a large area.

Yet another object of the invention is to provide an illuminator for photodynamic therapy which produces light in a selected wavelength region, for example, almost entirely in the 600 nm to 700 nm wavelength range.

According to a first aspect of the invention there is provided an illuminator for photodynamic therapy which includes a bulb and a filter assembly. The filter assembly includes the following components in an optical path: (1) a high-pass filter to filter out light having wavelengths below a first wavelength value; (2) a low-pass dichroic filter to filter out light having wavelengths above a second wavelength value; and (3) a dichroic mirror which reflects light having wavelengths between the first wavelength value and the second wavelength value and which transmits infrared light. An exit lens assembly directs light transmitted through the high-pass filter and the low-pass dichroic filter and reflected by the dichroic mirror onto a patient for photodynamic therapy.

According to a second aspect of the invention there is provided an illuminator for photodynamic therapy which includes a bulb to produce non-coherent light and a spherical condensing mirror located behind the bulb. A lens assembly is located along an optical path to produce an image of light from the bulb and the spherical condensing mirror. A dichroic filter, located along the optical path, filters out light having wavelengths above approximately 700 nanometers. A dichroic mirror, located along the optical path, reflects light having wavelengths below approximately 700 nanometers and transmits infrared light. A filter, located along the optical path, filters out light having wavelengths below approximately 600 nanometers. An exit lens assembly having at least one Fresnel lens is located along the optical path to direct light having wavelengths between 600 nanometers and 700 nanometers onto a patient. The illuminator also may include a heat dissipator located to receive infrared light transmitted by the dichroic mirror to dissipate incident infrared light as heat.

According to a third aspect of the invention there is provided a method of photodynamic therapy which includes the steps of: (a) providing light in a selected wavelength region, for example, between 600 nanometers and 700 nanometers; (b) energizing a bulb; (c) passing light through a high-pass filter having a cutoff at a wavelength of, for example, about 600 nanometers and through a low-pass dichroic filter having a cutoff at a wavelength of, for example, about 700 nanometers; (d) removing infrared wavelengths using a dichroic mirror which reflects non-infrared light and which transmits infrared light; and (e) directing light transmitted through the high-pass filter and the low-pass dichroic filter and reflected by the dichroic mirror to the patient to activate a light activable drug, including its prodrugs and metabolites.

According to a fourth aspect of the invention there is provided an illuminator for providing a uniform beam to a patient for photodynamic therapy. The illuminator includes a bulb having a filament, a condenser lens assembly, and an exit lens assembly. The condenser lens assembly images light from the bulb onto a plane lying in a region which includes the exit lens assembly and the space between the exit lens assembly and the patient but excludes the patient. The exit lens assembly images a virtual image of the condenser lens assembly onto the patient.

Other objects, features, and advantages of the invention will become apparent from the detailed description of preferred embodiments of the invention set forth below.

BRIEF DESCRIPTION OF THE DRAWINGS

Preferred embodiments of the invention will be described in detail below with reference to the accompanying drawings, wherein.

DETAILED DESCRIPTION OF PREFERRED EMBODIMENTS

The invention provides an illuminator for photodynamic therapy which permits radiation treatment including diagnosis of a large region of a patient with a high-powered uniform beam. The invention can be used, for example, to treat an area between 10 cm and 20 cm in diameter with light having wavelengths between about 600 nm and about 700 nm with high intensity and spectral uniformity. The illuminator conveniently provides approximately 1 to 60 mW/cm$^2$ of light which results in doses in the 600 nm to 700 nm region on the order of 100 J/cm$^2$. At the same time, the illuminator is small and lightweight.

Figure 1:
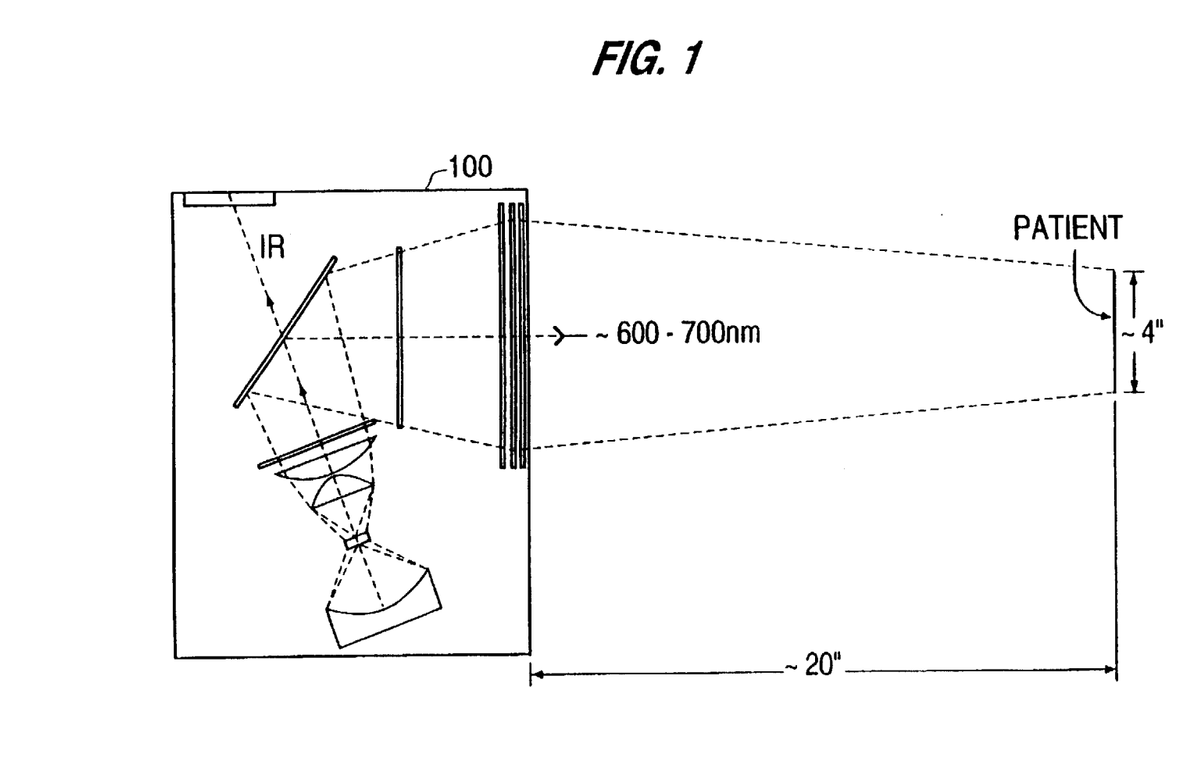
FIG. 1 illustrates an overall arrangement for conducting photodynamic therapy in accordance with a preferred embodiment of the invention.

FIG. 1 illustrates an overall arrangement for conducting photodynamic therapy in accordance with a preferred embodiment of the invention. As illustrated in FIG. 1, an illuminator 100 is located approximately 20 inches away from a patient who has been administered a photo-activable drug which accumulates in the target tissue. In this embodiment, the illuminator 100 is approximately 16 inches by 12 inches (41 cm to 30 cm, respectively) in cross-section. The illuminator 100 produces light having wavelengths between approximately 600 nm and 700 nm and shines this light on the patient over an area approximately 10 cm to 20 cm in diameter. Light in this wavelength range is reddish-orange to dark red in color. The light in turn causes chemical and/or biological changes in the drug to selectively activate, destroy or alter the drug in target tissue.

Figure 2:
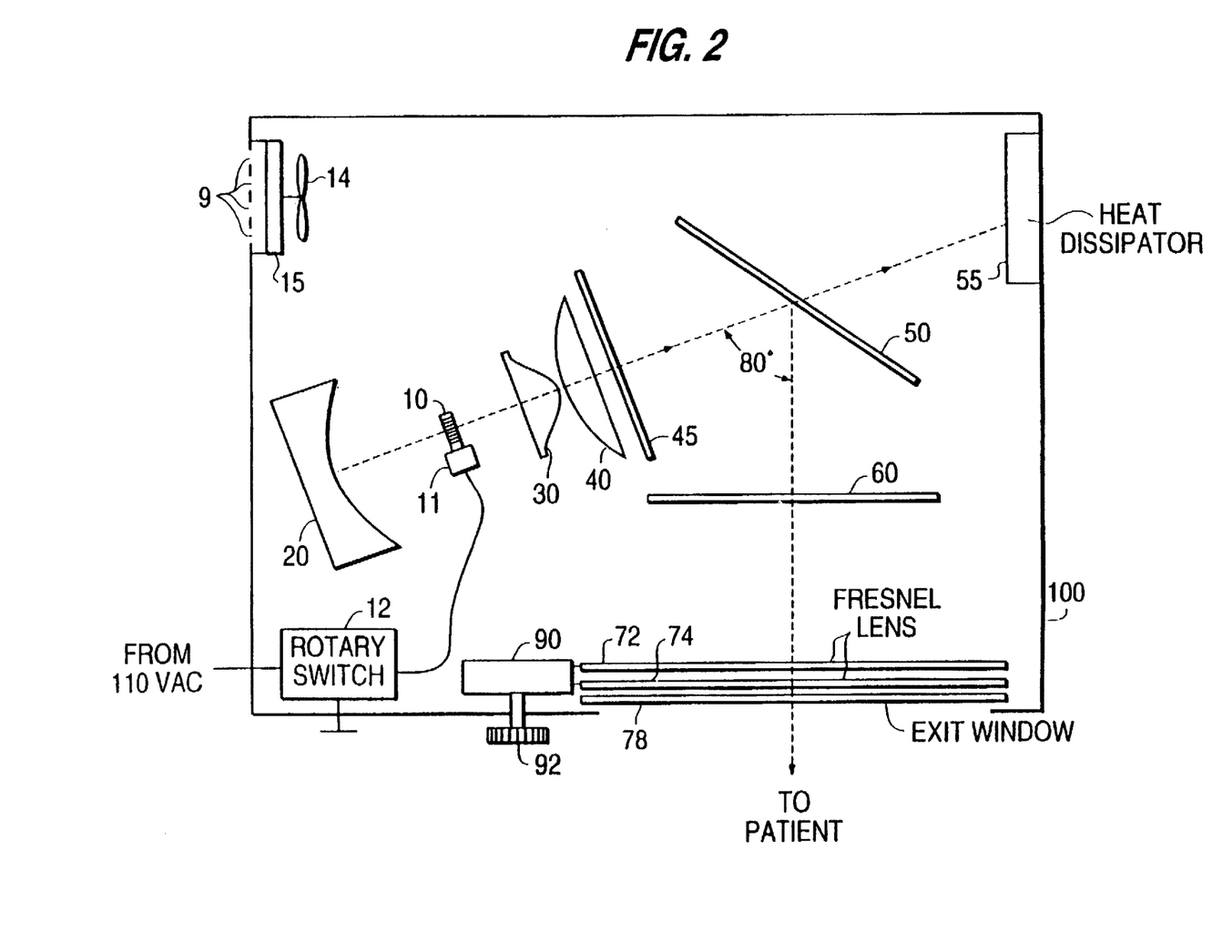
FIG. 2 illustrates a detailed design for the illuminator of FIG. 1.

FIG. 2 illustrates a detailed design for the illuminator 100 of FIG. 1. As illustrated in FIG. 2, the illuminator 100 includes a 1000 watt quartz tungsten-halogen (QTH) bulb 10, held in a holder 11, as a non-coherent unpolarized light source. The bulb 10 has a type CC-8 filament, is approximately 18 mm (millimeters)×7 mm, and is powered by a standard 110 VAC power source. The output power of the bulb 10 is controlled by controlling the power delivered to the bulb using a rotary switch 12.

Figure 3:
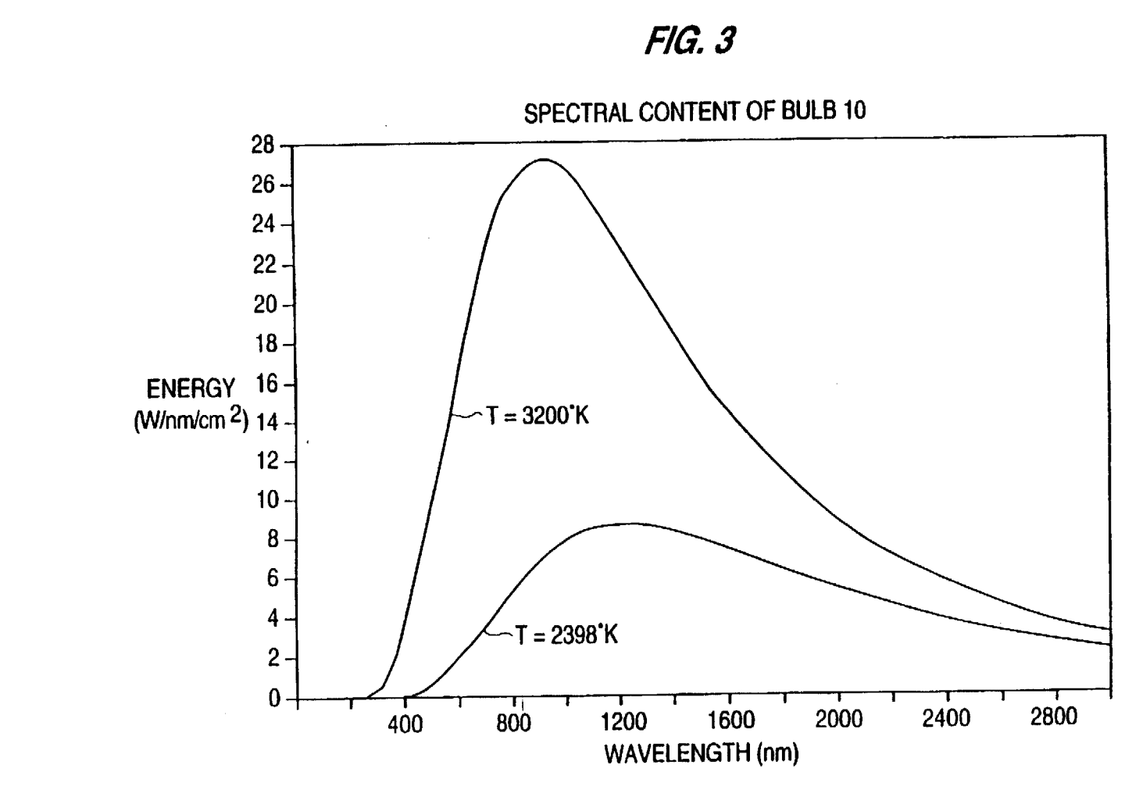
FIG. 3 is a graph showing the spectral content of bulb 10 of FIG. 2.

A tungsten-halogen bulb is used because it can operate on standard AC power and is inexpensive. Because bulb 10 can operate on standard AC power, additional power supplies are not required. Additionally, use of this bulb permits the illuminator to start up instantaneously and produce a continuous output with no sharp spectral lines. Bulb 10 essentially emits as a black body. FIG. 3 illustrates theoretical curves for the spectral content of bulb 10 and indicates that most of the energy of the bulb is emitted in the infrared region above 700 nm.

Figure 4:
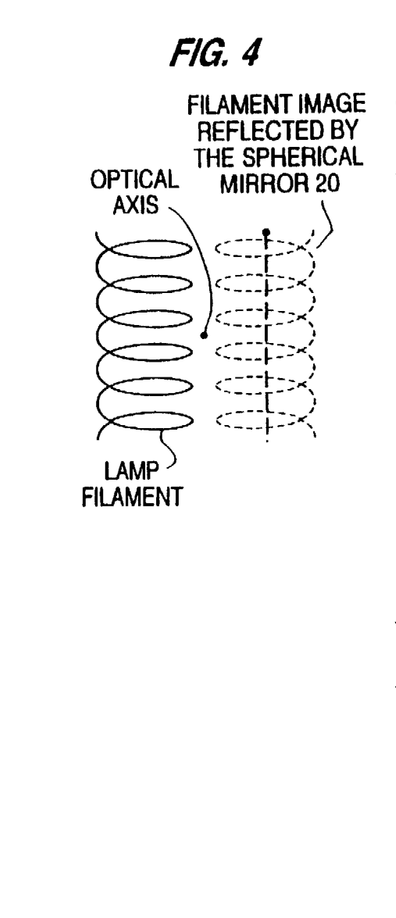
FIG. 4 illustrates the image produced by mirror 20 of FIG. 2.

A spherical condensing mirror 20 is placed behind the bulb 10 to produce an image of the filament parallel and beside the filament, as shown in FIG. 4, to create a bright, approximately square source of light, to increase the amount of light directed at the patient, and to increase lamp life for a given output. The bulb 10 is positioned slightly off-axis with respect to the optical axis of the mirror 20 so that the bulb and its image are symmetrically positioned about the optical axis of the mirror. Bulb 10 and mirror 20 together produce an uncollimated beam.

High boron content borosilica glass condensers 30 and 40 image the light from bulb 10 and mirror 20 onto the exit lens assembly (to be described below) or between the exit lens assembly and the patient, but not onto the patient. The first condenser 30 is an aspheric lens and the second condenser 40 is a plano-convex lens. This arrangement minimizes the size of the illuminator and provides lens diameters necessary to achieve the desired illumination area on the patient.

Figure 5:
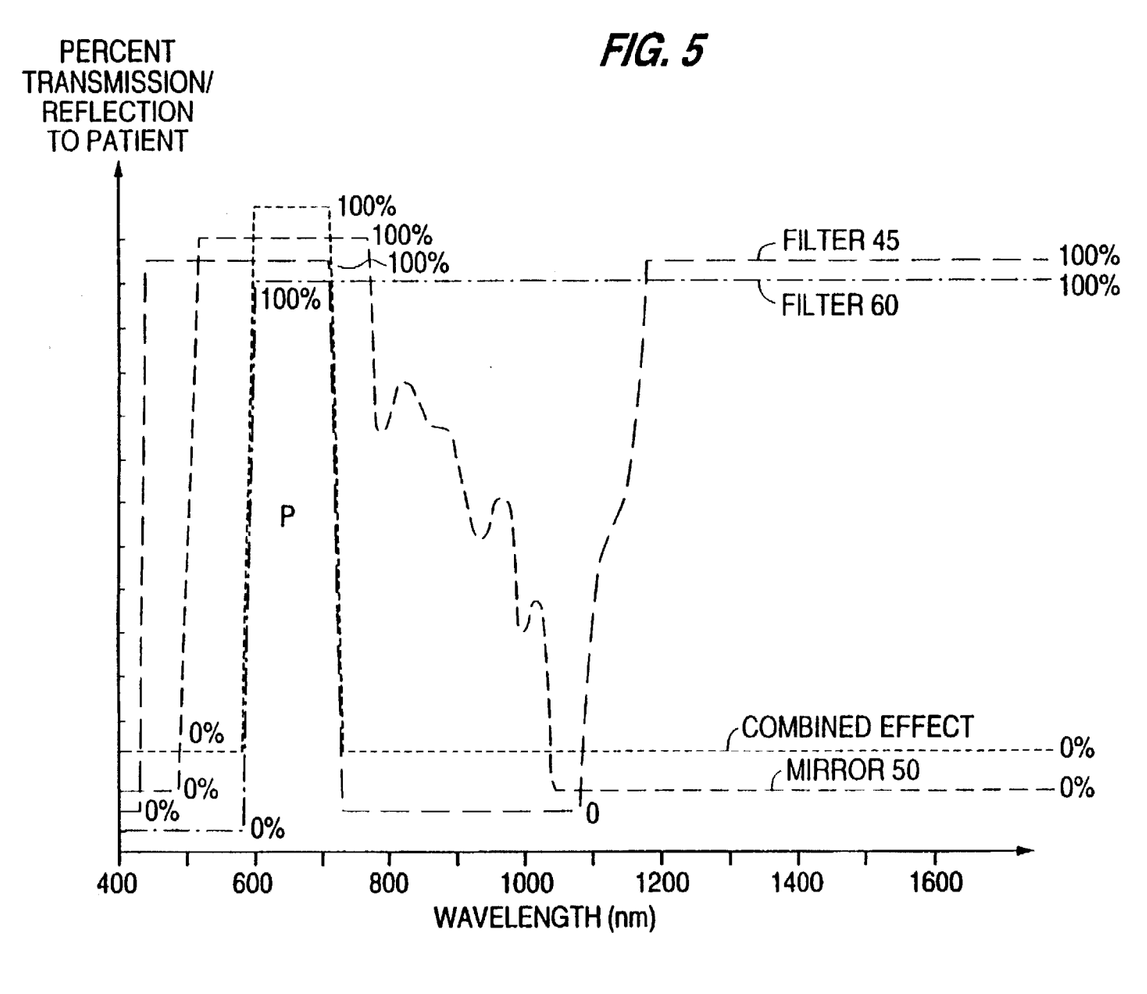
FIG. 5 illustrates combined transmission/reflection versus wavelength characteristics for filters 45 and 60 and mirror 50 of FIG. 2.

Radiation from the near ultraviolet ("UV") region to the near infrared region that is emitted by the bulb 10 is conditioned by filters 45 and 60 and mirror 50 which together ensure that the light provided to the patient is between about 600 nm and about 700 nm. FIG. 5 illustrates the combined percent of transmission or reflection to the patient versus wavelength characteristics for filters 45 and 60 and mirror 50. In this figure the horizontal axes corresponding to 0% are displaced a small amount to allow a better view of the characteristics for each component. As illustrated in FIG. 5, the combined effect of these elements is to create a window P between 600 nm and 700 nm and to filter out light outside of this window P. As indicated by FIG. 5, transmission in the 600 nm to 700 nm region is essentially 100%, except for reflection losses. Thus, virtually all of the light generated in this region by bulb 10 goes onto the patient for treatment purposes. The detailed properties and characteristics of each of these elements will be described below in turn.

Figure 6:
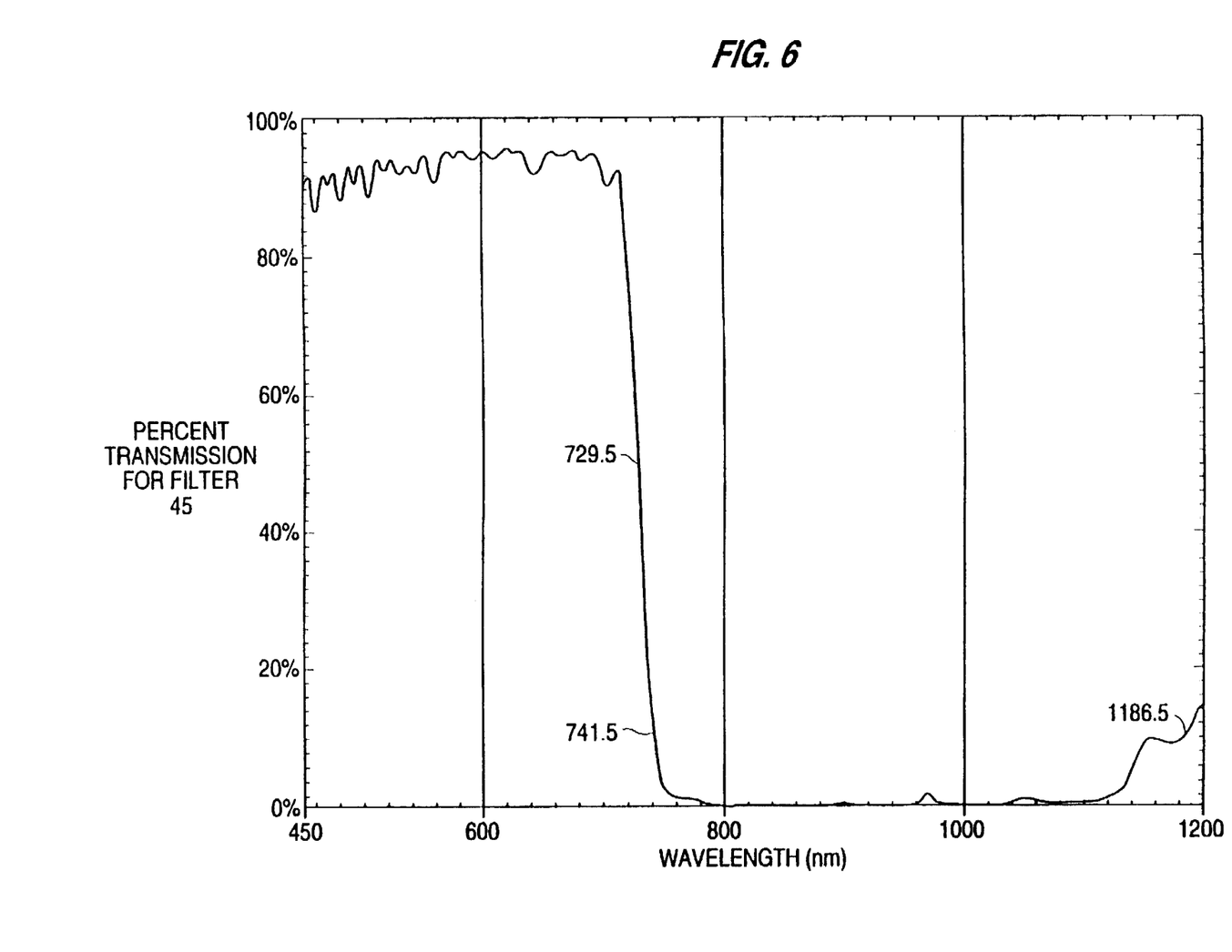
FIG. 6 illustrates percent transmission versus wavelength characteristics for filter 45 of FIG. 2.

Dichroic filter 45 in the beam path transmits light below about 720 nm, and thus transmits 600 nm to 700 nm light, while filtering out light between 720 nm and approximately 1100 nm. This filtering is accomplished by reflecting the unwanted wavelengths. FIG. 6 illustrates percent transmission versus wavelength characteristics for filter 45. Filter 45 determines the high wavelength cutoff (about 700 nm).

The use of a dichroic for filter 45 presents several advantages over an absorption type filter. Since the dichroic does not absorb light, it can tolerate much higher intensities than absorption type filters. This is important in this case because filter 45 directly receives a large percentage of the bulb output. Bulk absorption filters which eliminate infrared exist, but, if used in this position would break due to excessive heat absorption. A bulk absorption filter could be put in the exit assembly (where filter 60 is) for high wavelength cutoff, however, because it would still absorb a significant portion of the bulb output at this position, it would still heat up considerably and either break or melt the plastic Fresnel lenses in the exit assembly unless very aggressive cooling was provided.

More importantly, bulk absorption filters which are designed for high wavelength cutoff have a very gradual decrease in transmission as a function of wavelength. Filters strong (opaque) enough to fully absorb the infrared would cause a significant loss of power in the spectral region of interest (600 to 700 nm). Filters which provide enough power in the spectral region of interest would leak too much infrared to the patient. The sharp cutoff of the dichroic allows the illuminator to filter out virtually all (greater than 90%) of the infrared while at the same time transmit virtually all (greater than 90%) of the light in the 600 nm to 700 nm region.

Ideally, filter 45 should have a very sharp cutoff at 700 nm without attenuating any light below 700 nm. As illustrated in FIG. 6, filter 45 starts transmitting again at around 1100 nm. All dichroic filters have this property of retransmitting at a wavelength longer than a certain wavelength. The dichroic mirror 50 ensures that radiation above 1100 nm does not reach the patient.

Figure 7:
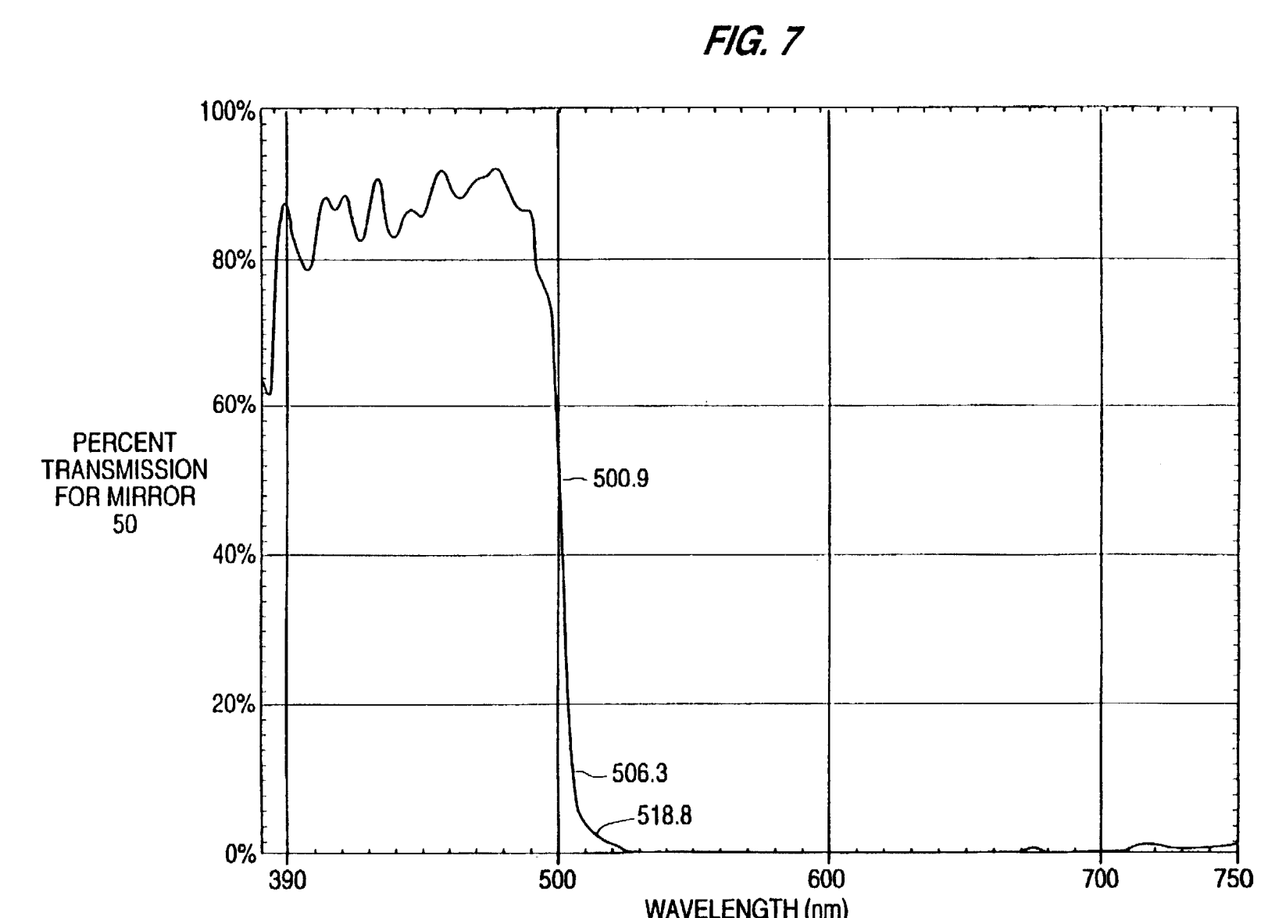
FIG. 7 illustrates percent transmission versus wavelength characteristics for mirror 50 of FIG. 2.

Dichroic mirror 50 operates in the reflecting mode to transmit infrared radiation to a heat dissipator 55 (to be described below) and to reflect radiation between 600 nm and 700 nm to the exit lens assembly. Thus, mirror 50 is used to "dump" infrared radiation away from the patient. FIG. 5 illustrates the percent of light which is reflected to the patient by mirror 50 for various wavelengths. As illustrated in FIG. 5, light in the 600 nm to 700 nm region is reflected to the patient. At about 750 nm mirror 50 begins to dump the light to heat dissipator 55. FIG. 7 illustrates transmission versus wavelength characteristics for mirror 50 near the low cutoff point. As can be seen from FIG. 7, at about 500 nm most of the incident light is not transmitted to heat dissipator 55 but is instead reflected to the patient.

Figure 8:
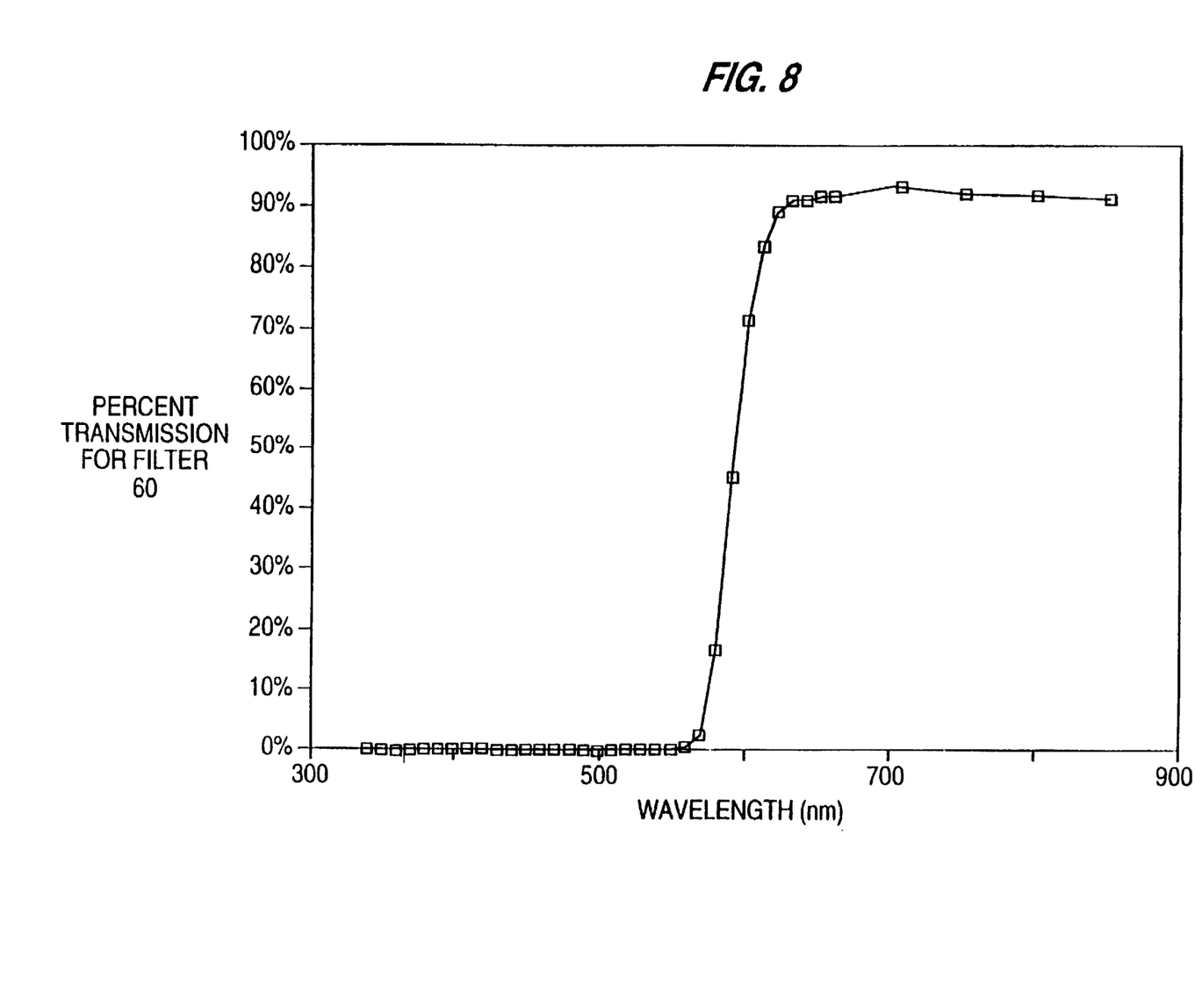
FIG. 8 illustrates percent transmission versus wavelength characteristics for filter 60 of FIG. 2.

A long-wavelength-pass acrylic filter 60 filters out violet and ultraviolet light. Filter 60 is a bulk absorption-type filter which absorbs short wavelengths and transmits long wavelengths. In this embodiment, filter 60 is a number 2226 filter manufactured by Rohm and Haas. FIG. 8 illustrates the transmission versus wavelength characteristics for filter 60. Ideally filter 60 should have a very sharp cutoff at 600 nm without attenuating light above 600 nm. Filter 60 has a 50% cutoff point at 590 nm and a half-width (10 to 90% transmission) of approximately 20 nm. Thus, at 600 nm 90% of the incident light is transmitted.

Correct matching of filter 45, mirror 50, and filter 60 is important. In the illuminator 100 the light is not collimated, i.e., not parallel. When light reaches a dichroic surface (e.g., filter 45 or mirror 50) the cutoff wavelength between reflection and transmission depends slightly on the angle of incidence when the surface is roughly perpendicular to the incoming light, as is the case for filter 45. This dependence is much greater when the dichroic surface is not perpendicular to the central ray, as is the case for mirror 50. This is one reason why the cutoffs of mirror 50 are not used to delimit the 600 nm to 700 nm band. If mirror 50 were used to delimit the desired band, there would be color variation in the light provided to the patient due to slight changes in the angle of incidence with respect to mirror 50.

Figure 9:
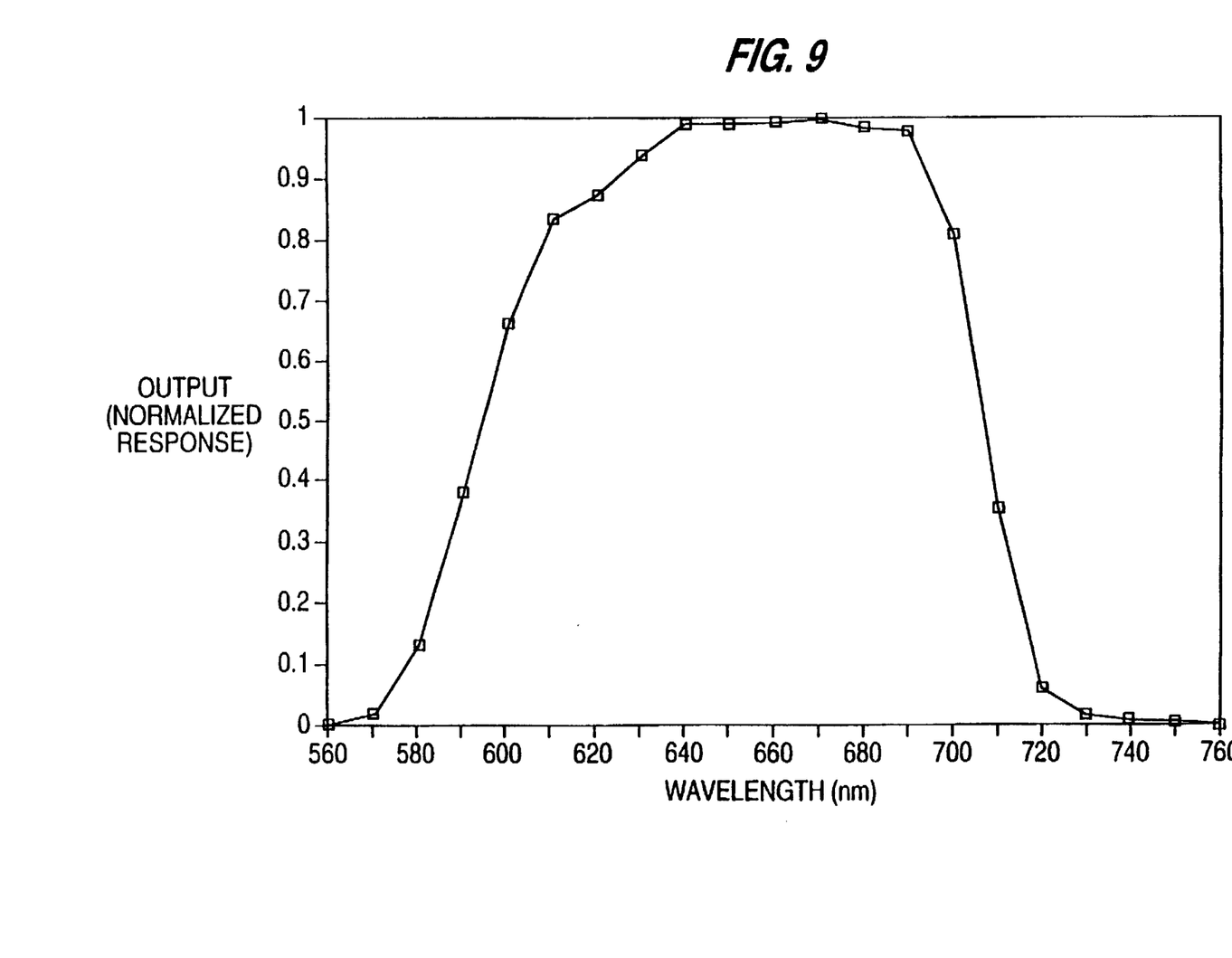
FIG. 9 illustrates overall output versus wavelength characteristics for illuminator 100 of FIG. 2.
Figure 10:
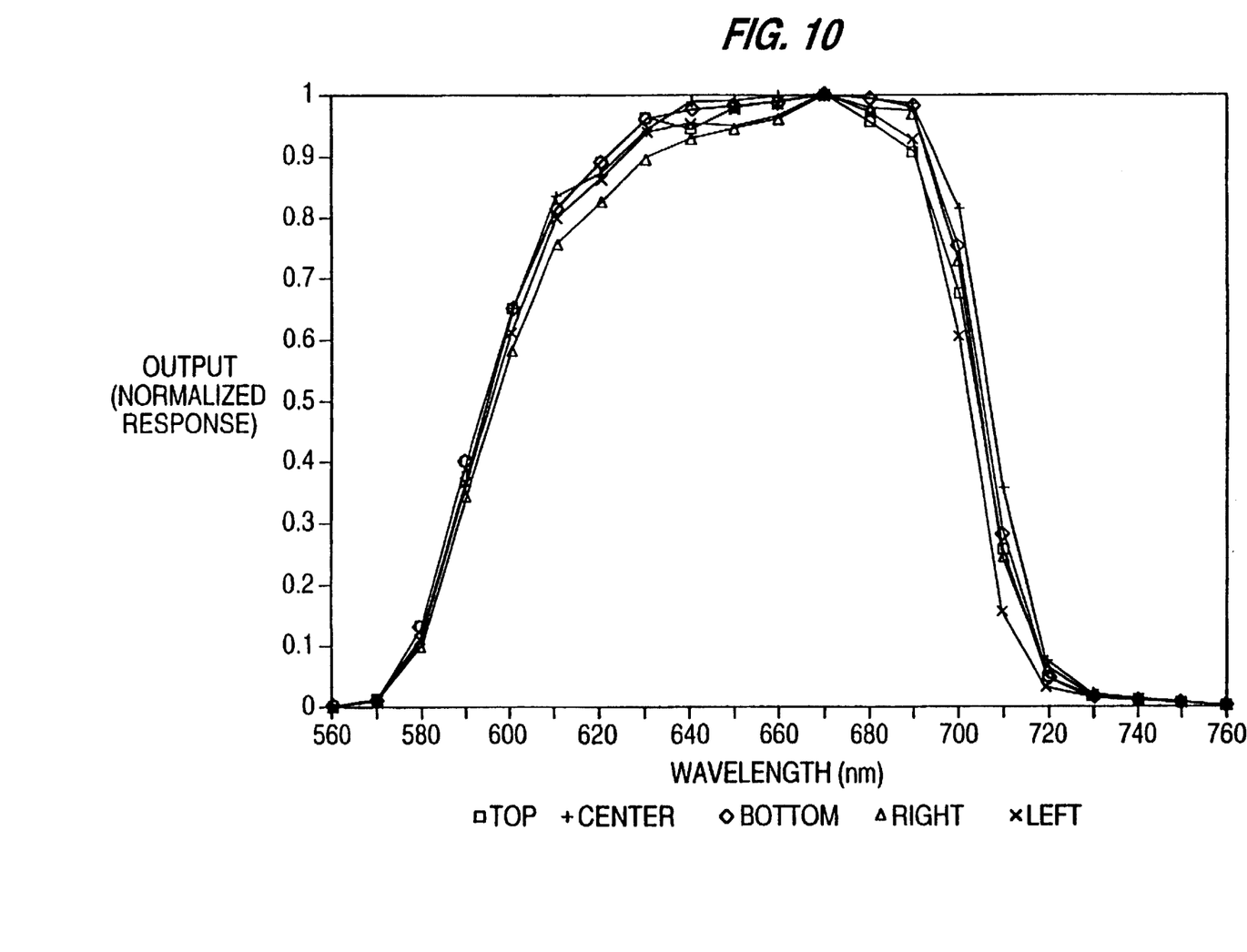
FIG. 10 illustrates output versus wavelength characteristics at different positions within the illuminated area for illuminator 100 of FIG. 2.

FIGS. 9 and 10 illustrate output versus wavelength characteristics for illuminator 100. FIG. 9 illustrates overall output versus wavelength characteristics. FIG. 10 illustrates spectral characteristics measured at different positions within an illuminated area. The different curves in FIG. 10 correspond to five positions with respect to a 10 cm circle on the patient: one at the center and the other four at the edges in a square pattern. Both high and low wavelength cutoff total variations are within approximately 3 nm. This illustrates the excellent spectral, or color, uniformity obtained with the filter set described above (i.e., on the order of 0.5% of the total range). As will be appreciated from these figures, illuminator 100 produces a very uniform output over the desired range of 600 nm to 700 nm while projecting virtually no radiation outside of the desired range.

The exit lens assembly includes two acrylic Fresnel lenses 72 and 74. The exit lens assembly images the virtual image of lens 30 and lens 40 onto the patient. The optical system formed by mirror 20, aspheric lens 30, lens 40 and Fresnel lenses 72 and 74 is designed to produce light having a uniform intensity within the illuminated area. One of the objects of this invention is to provide uniform illumination using a filament type light bulb such as a tungsten halogen lamp because of the advantages of low initial and maintenance costs and easy starting and operation associated with these types of bulbs. For this type of light source, simply collimating the beam is not adequate to achieve uniformity as is the case for sources with small emitting areas, such as arc lamps. The large size of the filament makes it virtually impossible to provide perfect collimation. A pseudo collimated beam (i.e., one where the center rays of the cones of light at any point in the beam are parallel) would be very non-uniform and have a very large divergence, like a poorly designed flashlight.

Figure 11:
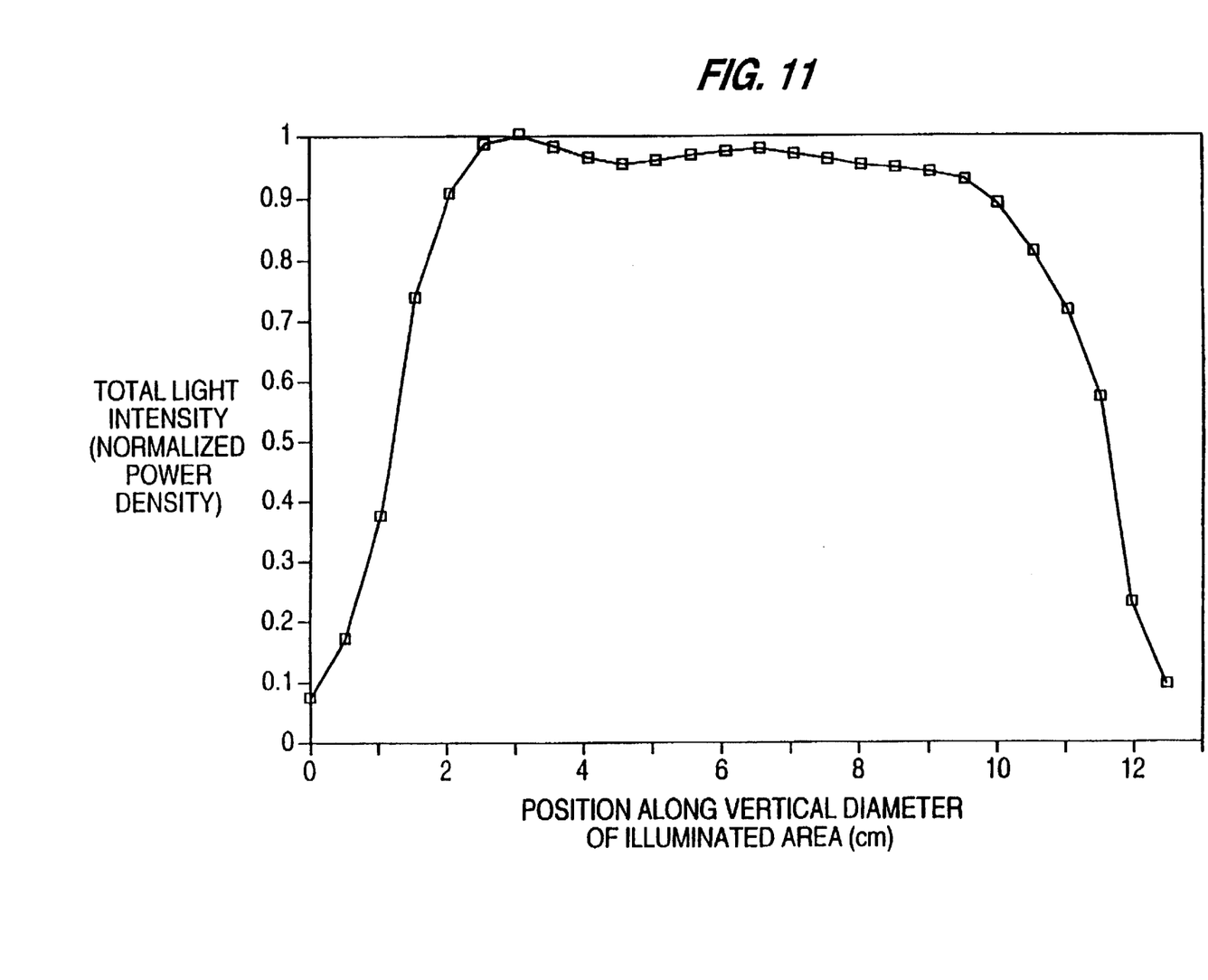
FIG. 11 illustrates total light intensity measured at different positions along the vertical diameter of an illuminated area for the illuminator 100 of FIG. 2.

FIG. 11 illustrates the total light intensity measured along the vertical diameter of an illuminated area on the patient (at a distance of 52 cm). These measurements demonstrate that the optical system of illuminator 100 produces a beam highly uniform in total intensity. This highly uniform intensity results from the optics scrambling the image of the filament such that an image of the filament is not reproduced on the patient. In other words, the spatial variation of light on the patient is much more uniform than the spatial variation of light from the bulb.

A mechanical assembly 90 and a spot diameter control knob 92 are provided to move lenses 72 and 74 over a range of about 8 cm to vary the spot diameter between 10 cm and 20 cm. The exit lens assembly provides a very uniform beam within a well-defined illuminated area at the position of focus on the patient. A tempered glass exit window 78 protects the Fresnel lenses, seals the housing, and shields the operator and the patient from hot components. In this embodiment, all of the optics other than the bulb 10 are coated with a conventional anti-reflection material to minimize reflection losses.

The infrared light which is transmitted through mirror 50 strikes internal heat dissipator 55, which converts the infrared light into heat. Heat dissipator 55 is provided with holes which serve as the exhaust for cooling air drawn into the illuminator housing by a fan 14 (illustrated diagrammatically in FIG. 2) through holes 9 and foam filter 15. The passage of cooling air through the holes in heat dissipator 55 removes the heat generated in heat dissipator 55.

The bulb 10 produces a relatively large amount of light. At such power levels even a small percentage of infrared radiation would burn the patient if not virtually totally eliminated. The above design ensures that the patient is treated with high-powered light which is virtually free of infrared components.

The fan 14 cools the optics and the housing for the optics. Foam filter 15 on the input side of the fan minimizes the accumulation of particles on the optical elements. Internal tunnels and baffles (not shown) direct cool air to the high temperature areas and prevent the temperature of the housing itself and the exhaust air from exceeding 30° C. over ambient temperature. A temperature sensor (not shown) ensures that the fan operates when the illuminator is hot.

Medical instrumentation which uses light can cause eye damage if maximum radiance levels are exceeded and can cause hyperthermia if maximum radiant flux density levels are exceeded. The invention ensures that there is no danger from either. The maximum radiance at any position is approximately 5 W/[cm$^2$*Sr], which is more than an order of magnitude lower than ophthalmologic lamps. The maximum flux density at any position is 100 mW/cm$^2$, which is low enough to prevent hyperthermia.

If a bright, very small spot source on the order of a few millimeters (e.g., a Xe lamp) were used with this optical layout, levels of optical radiation intensity would occur in some regions outside of the illuminator which would be dangerous to both the operator and the patient. This illuminator is specifically designed to be used with a large, extended light source such as a filament. This type of danger also exists with laser sources unless the illuminator is arranged to diffuse the beam without losing too much radiation.

The illuminator 100 outputs between 55 and 65 mW/cm$^2$ when the spot diameter is 10 cm and between 17 and 20 mW/cm$^2$ when the spot diameter is 20 cm. Because the total light throughput is constant, the intensity is inversely proportional to the square of the illuminated spot diameter. At the same time, the distance of the most uniform illumination area from exit window 78 varies with the spot diameter. The following Table 1 shows the optimum distance between the patient and the exit window 78 to achieve the most uniform illumination at the patient as a function of spot diameter.

TABLE 1

Optimum Illuminator-Patient Distance
for the Most Uniform Illumination

| Illuminated Diameter (cm) | Distance Between Illuminator and Patient (cm) |
| --- | --- |
| 10 | 52 |
| 11 | 53 |
| 13 | 57 |
| 15 | 61 |
| 17 | 66 |
| 20 | 76 |

The following Table 2 sets forth detailed construction data for one implementation of the invention. This implementation delivers 7 W (Watts) of power in a 10 cm spot at a distance of 52 cm.

TABLE 2

Detailed Construction Data

| Bulb 10 | |
| --- | --- |
| Power | 1000 W |
| Filament Length | 18 mm |
| Filament Width | 7 mm |
| Power 600–700 nm | 47 W |
| Mirror 20 | |
| Radius | 60 mm |
| Thickness at the center | 4 mm |
| Lens 30 | |
| Distance from Filament | 25 mm |
| Diameter | 58 mm |
| Focal Length | 39 mm |
| Thickness | 27.5 mm |
| Lens 40 | |
| Distance Between Lens 30 and Lens 40 | 5 mm |
| Diameter | 89 mm |
| Length Focal | 308 mm |
| Center Thickness | 8.4 mm |
| Edge Thickness | 3 mm |
| Filter 45 | |
| Distance From Lens 40 | 10 mm |
| Thickness | 4–6 mm |
| Refraction Index | 1.47 |
| Square Side | 100 mm |
| Filter 50 | |
| Distance to Lens 40 | 100 mm |
| Thickness | 6 mm |
| Refraction Index | 1.47 |
| Height | 116 mm |
| Angle of Normal to Beam Center | 40° |
| Width | 151 mm |
| Filter 60 | |
| Path Distance From Lens 40 | 170 mm |
| Diameter | 139 mm |
| Fresnel Lens 72 | |
| Path Distance from Lens 40 | 310 mm |
| Focal Length | 354 mm |
| Diameter | 226 mm |
| Thickness | 2.8 mm |
| Fresnel Lens 74 | |
| Distance Between Lens 72 and Lens 74 | 5 mm |
| Focal Length | 610 mm |
| Diameter | 226 mm |
| Window 78 | |
| Distance Between Lens 74 and Window 78 | 5 mm |
| Diameter | 226 mm |
| Thickness | 6 mm |

To prevent damage due to thermal stress in the situation where the illuminator is unplugged while it is operating at full power, the optics and filters near the bulb 10 are made of heat resistant low-thermal-expansion glass and are mounted with high temperature plastic fasteners or high temperature flexible adhesive to minimize thermally induced mechanical stresses. The acrylic components, i.e., filter 60 and Fresnel lenses 72 and 74, have a long term maximum operating temperature of 80° C. and a short term maximum temperature of 96° C. To ensure that these temperatures are not reached even when the lamp is unplugged while in operation, these components are mounted far from the bulb and are protected by internal baffles. Thus, even the heat soak from an unplugged system will not raise the temperature of the acrylic components above their allowable limits.

Although the invention has been described above by reference to certain preferred embodiments of the invention, the invention is not limited to the preferred embodiments set forth above. Other designs, variations, applications, and modifications will occur to those skilled in the art after receiving the above teachings.

By way of example, it is understood that the arrangement of the filters can be varied. For example, light could first be passed through a reflecting dichroic mirror (e.g., mirror 50), then through a long pass bulk filter (e.g., filter 60), then through a transmitting dichroic filter (e.g., filter 45). Or, light could be passed through a long pass bulk filter (e.g., filter 60), then through a transmitting dichroic filter (e.g., filter 45), and then through a reflecting dichroic mirror (e.g., mirror 50). The Fresnel lenses can be replaced with a standard glass lens or lenses. A collimated beam may be acceptable in certain applications even though use of a collimated beam would result in a less uniform radiation pattern and a worse depth of focus. Alternatively, the illuminator could be used to direct light of a wavelength that causes the drug to fluoresce and then be detected by conventional means. The scope of the invention is therefore defined by reference to the following claims.

What is claimed is:

1. An illuminator for photodynamic therapy, comprising:
   (a) a bulb holder; and
   (b) a filter assembly which includes the following components in an optical path
      (1) a high-pass filter to filter out light having wavelengths below a first wavelength value;
      (2) a low-pass dichroic filter to filter out light having wavelengths above a second wavelength value; and
      (3) a dichroic mirror which reflects light having wavelengths between the first wavelength value and the second wavelength value and which transmits infrared light; and
   (c) an exit assembly to direct light transmitted through the high-pass filter and the low-pass dichroic filter and reflected by the dichroic mirror onto a patient;
   wherein the exit assembly includes a Fresnel lens and wherein the illuminator includes a mechanism to move the Fresnel lens to vary a spot size on the patient.

2. An illuminator to provide a uniform beam to a patient for photodynamic therapy, the illuminator comprising:
   (a) a bulb holder for holding a bulb having a filament;
   (b) a condenser lens assembly; and
   (c) an exit lens assembly; wherein the condenser lens assembly images light from the bulb onto a plane lying in a region which excludes the patient, and
   the exit lens assembly images a virtual image of the condenser lens assembly output other than an image of the filament onto the patient.

3. An illuminator as set forth in claim 2 wherein the condenser lens assembly includes an aspheric lens.

4. An illuminator as set forth in claim 2 wherein the condenser lens assembly includes a plano convex lens.

5. An illuminator as set forth in claim 2 further comprising a spherical condensing mirror, located behind the bulb holder, to produce an off-axis image of the filament to provide a uniform source of light.

6. An illuminator as set forth in claim 2 further comprising an optical element, located behind the bulb holder, to produce an off-axis image of the filament to provide a uniform source of light.

7. An illuminator for photodynamic therapy, comprising:
   (a) a bulb holder; and
   (b) a filter assembly which includes the following components in an optical path
      (1) a high-pass filter to filter out light having wavelengths below a first wavelength value;
      (2) a low-pass dichroic filter to filter out light having wavelengths above a second wavelength value; and
      (3) a dichroic mirror which reflects light having wavelengths between the first wavelength value and the second wavelength value and which transmits infrared light;
   (c) an exit assembly to direct light transmitted through the high-pass filter and the low-pass dichroic filter and reflected by the dichroic mirror onto a patient; and
   (d) a spherical condensing mirror, located behind the bulb holder, to produce an off-axis image of a bulb filament to provide a uniform source of light.

8. An illuminator for photodynamic therapy, comprising:
   (a) a bulb to produce non-coherent light;
   (b) a spherical condensing mirror located behind the bulb;
   (c) a lens assembly, located along an optical path, to produce an image of light from the bulb and the spherical condensing mirror;
   (d) a dichroic filter, located along the optical path, to filter out light having wavelengths above approximately 700 nanometers;
   (e) a dichroic mirror, located along the optical path, to reflect light having wavelengths below approximately 700 nanometers and to transmit infrared light;
   (f) a filter, located alone the optical path, to filter out light having wavelengths below approximately 600 nanometers;
   (g) an exit assembly having a Fresnel lens, located along the optical path, to direct light having wavelengths between 600 nanometers and 700 nanometers onto a patient;
   wherein said spherical condensing mirror produces an off-axis image of a bulb filament to provide a uniform source of light.

9. An illuminator for photodynamic therapy, comprising:
   (a) a bulb holder; and
   (b) a filter assembly which includes the following components in an optical path
      (1) a high-pass filter to filter out light having wavelengths below a first wavelength value;
      (2) a low-pass dichroic filter to filter out light having wavelengths above a second wavelength value; and
      (3) a dichroic mirror which reflects light having wavelengths between the first wavelength value and the second wavelength value and which transmits infrared light;
   (c) an exit assembly to direct light transmitted through the high-pass filter and the low-pass dichroic filter and reflected by the dichroic mirror onto a patient; and
   (d) an optical element, located behind the bulb holder, to produce an off-axis image of a bulb filament to provide a uniform source of light.

10. An illuminator for photodynamic therapy, comprising:
    (a) a bulb to produce non-coherent light;
    (b) an optical element, located behind the bulb, to produce an off-axis image of a bulb filament to provide an off-axis image of a bulb filament to provide a uniform source of light;

(c) a lens assembly, located along an optical path, to produce an image of light from the bulb and the optical element;

(d) a dichroic filter, located along the optical path, to filter out light having wavelengths above approximately 700 nanometers;

(e) a dichroic mirror, located along the optical path, to reflect having wavelengths below approximately 700 nanometers and to transmit infrared light;

(f) a filter, located along the optical path, to filter out light having wavelengths below approximately 600 nanometers; and (g) an exit assembly having a Fresnel lens, located along the optical path, to direct light having wavelengths between 600 nanometers and 700 nanometers onto a patient.

* * * * *